(12) United States Patent
Kawamura et al.

(10) Patent No.: US 7,226,777 B2
(45) Date of Patent: Jun. 5, 2007

(54) TURBIDIMETRIC IMMUNOASSAY AND AN APPARATUS THEREFOR

(75) Inventors: Tatsurou Kawamura, Kyotanabe (JP); Keiko Yugawa, Nara (JP); Akihito Kamei, Yawata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/886,640

(22) Filed: Jul. 9, 2004

(65) Prior Publication Data

US 2005/0009102 A1    Jan. 13, 2005

(30) Foreign Application Priority Data

Jul. 9, 2003    (JP)    ............................. 2003-272357

(51) Int. Cl.
*C12M 1/34*    (2006.01)
*C12M 3/00*    (2006.01)

(52) U.S. Cl. ................. 435/288.7; 435/7.1; 435/283.1; 435/286.1; 435/287.2; 436/518; 356/300; 356/302

(58) Field of Classification Search .................... 435/4, 435/7.1, 283.1, 286.1, 287.2, 288.7; 436/501, 436/518; 422/50, 55, 61, 68.1; 356/300, 356/302
See application file for complete search history.

(56) References Cited

U.S. PATENT DOCUMENTS

| 4,486,530 | A | * | 12/1984 | David et al. ................ 435/7.91 |
| 4,843,021 | A | * | 6/1989 | Noguchi et al. ............. 436/533 |
| 5,371,021 | A |   | 12/1994 | Oh et al. |
| 5,420,042 | A | * | 5/1995 | Schafer et al. .............. 436/517 |
| 6,044,330 | A | * | 3/2000 | Patzke ......................... 702/32 |
| 6,210,975 | B1 | * | 4/2001 | Karl et al. ................... 436/518 |
| 6,248,597 | B1 | * | 6/2001 | Eda et al. .................... 436/518 |
| 6,284,472 | B1 | * | 9/2001 | Wei et al. ..................... 435/7.1 |
| 6,432,657 | B1 | * | 8/2002 | Kikuchi et al. ............... 435/13 |
| 6,548,310 | B1 | * | 4/2003 | Murata et al. ............... 436/518 |
| 6,750,966 | B2 | * | 6/2004 | Tucker ........................ 356/338 |
| 2003/0013129 | A1 | * | 1/2003 | Kawamura et al. ........... 435/7.1 |
| 2003/0100128 | A1 |   | 5/2003 | Kenjyou et al. |
| 2003/0219910 | A1 |   | 11/2003 | Yugawa et al. |
| 2005/0107959 | A1 | * | 5/2005 | Fukunaga et al. ............. 702/19 |

* cited by examiner

*Primary Examiner*—Long V. Le
*Assistant Examiner*—Melanie J. Yu
(74) *Attorney, Agent, or Firm*—McDermott Will & Emery LLP

(57) ABSTRACT

According to the present invention, the expansion of measurable concentration range for an antigen in a sample solution can be achieved, without a step of dilution or the like. The concentration of an antigen contained in a sample solution is determined from the maximum value and/or minimum value of turbidity level detected in the observation of the transient phenomenon of turbidity, elapsed time when the maximum and/or minimum value is observed, and turbidity level.

8 Claims, 13 Drawing Sheets

FIG. 22  SC90 measured value after 300 seconds
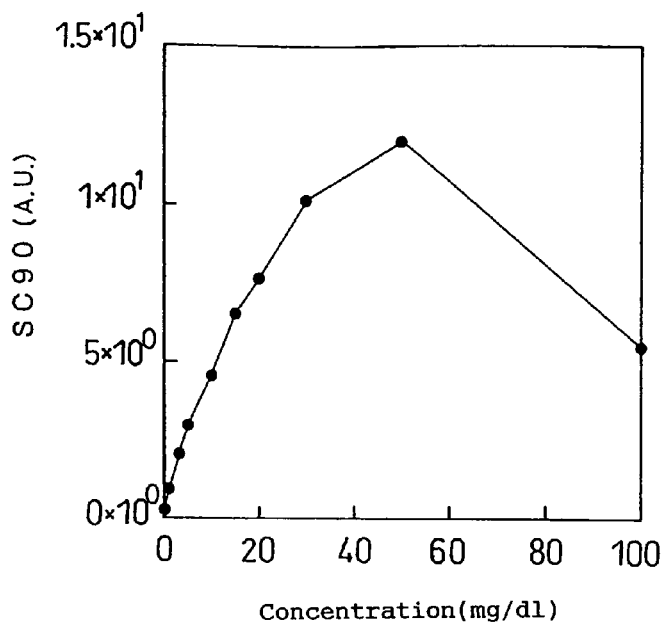
FIG. 23
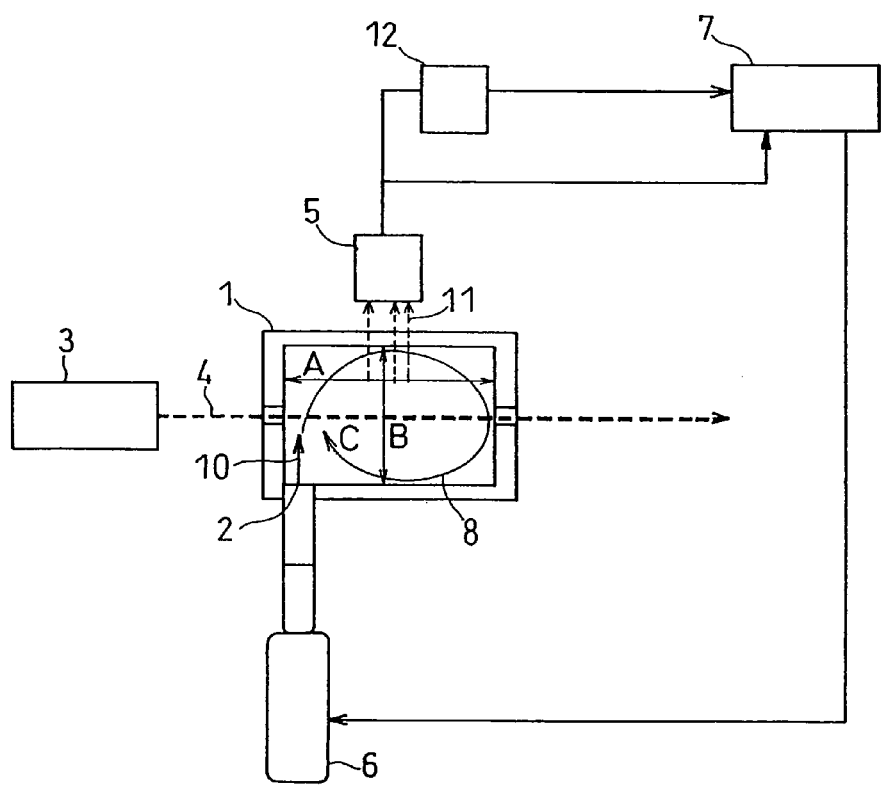

F I G. 2 4
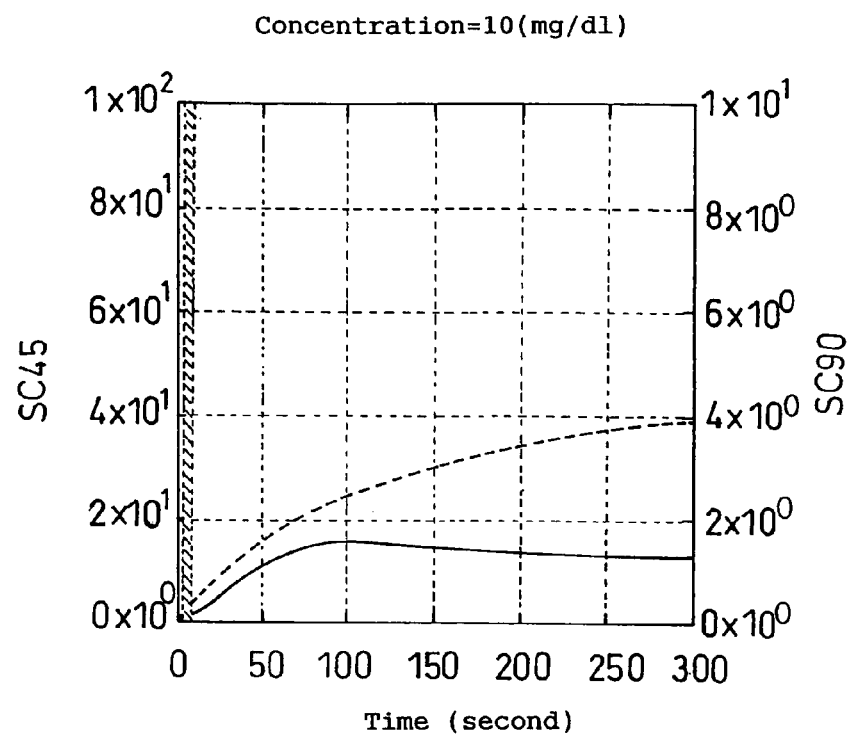
F I G. 2 5
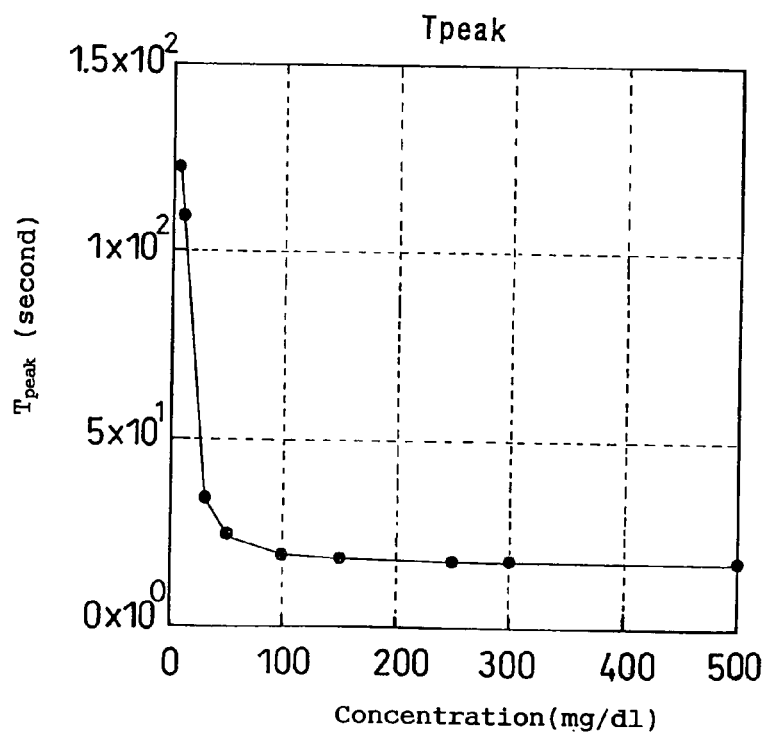

TURBIDIMETRIC IMMUNOASSAY AND AN APPARATUS THEREFOR

BACKGROUND OF THE INVENTION

The present invention relates to a turbidimetric immunoassay for measuring the concentration of an antigen dissolved in a sample solution and more particularly to a turbidimetric immunoassay for measuring the concentration of albumin contained in urine, and an apparatus therefor.

Conventional methods for measuring the concentration of an antigen involve: adding, to a sample solution, an antibody that specifically binds to an antigen contained in the sample solution to produce an antigen-antibody complex by an antigen-antibody reaction, which makes the sample solution turbid; and determining the concentration of the antigen from the turbidity of the sample solution. The turbidity is measured by directing light to the sample solution and then detecting scattered light generated in the solution or transmitted light having passed through the solution. When the turbidity increases, the intensity of the scattered light also increases, but the intensity of the transmitted light decreases.

In the above-described method, the measurement is made in a range where the molar concentration of the antibody is greater than that of the antigen and a range where they are almost equivalent, more specifically, in prozone A through B (hereinafter may be referred to as A-B range) and zone of equivalence C (hereinafter may be referred to as C range) as shown in FIG. 17. In FIG. 17, the turbidity increases as the concentration of the antigen increases in the A-B range whereas the variation of the turbidity with the concentration of the antigen is small in the C range. In the postzone D, the turbidity decreases as the concentration of the antigen is increased, which is called prozone phenomenon. Accordingly, in the above method, the concentration of the antigen is determined by creating a calibration line in the A-B range of FIG. 17 and calculating it from a measured turbidity level based on the calibration curve.

As described above, the concentration of the antigen should be in the prozone A-B or the zone of equivalence C in order for the measurement to be made, and therefore the antibody concentration is required to be increased. In such case, sensitivity in a low concentration range is sometimes sacrificed. Moreover, in order to check that the concentration of the antigen is actually not in the postzone D (i.e. D range of FIG. 17), a step of diluting the sample solution or a step of adding additional amount of antibody has to be done. In the case of using a sample solution whose antigen concentration may be in the D range, two concentrations are obtained from measured turbidity levels. For this reason, it is necessary to check that the concentration of the antigen is not in the D range (see US2003-219910 A1 and US2003-100128 A1).

SUMMARY OF THE INVENTION

An object of the present invention is to solve the above problems encountered in the turbidimetric immunoassay and expand the measurable concentration range for an antigen in a sample solution without sacrifice of sensitivity in a low concentration range. Another object of the present invention is to provide a turbidimetric immunoassay free of a step of diluting a sample solution or a step of adding additional amount of antibody for checking that the concentration of the antigen is not in the postzone, i.e. the D range of FIG. 17.

In a turbidimetric immunoassay according to the present invention, a sample solution containing an antigen as the analyte is first mixed with a reagent containing an antibody that specifically binds to the analyte to yield a mixed solution. Due to the specific binding reaction, an antigen-antibody complex is produced, which increases the turbidity of the sample solution.

The turbidity level of the obtained mixed solution is then measured discretely a plurality of times or consecutively, and then the correlation of the obtained turbidity level and elapsed time after the mixing is determined. Based on the correlation, the maximum or minimum value of the measured turbidity level ($S_{peak}$) is detected to determine elapsed time when the $S_{peak}$ is observed ($T_{peak}$).

By doing these steps, the variation in the turbidity level is examined to check whether the prozone phenomenon occurs in the sample solution with the variation, and the concentration of the analyte is determined by the presence or absence of the prozone phenomenon.

The turbidity level in the step (2) is preferably measured by scattered light, and the maximum value is preferably detected in the step (4).

In another embodiment, the concentration of the analyte is preferably determined from the correlation between the $S_{peak}$ and the $T_{peak}$.

In another embodiment, the concentration of the analyte is preferably determined from the correlation between the elapsed time $T_{peak}$ and the measured turbidity level $S(T)$ after a certain length of time T after the mixing. In this case, $T>T_{peak}$ is preferably satisfied.

In another embodiment, $S_{peak}$ as well as the $T_{peak}$ when the $S_{peak}$ is observed are preferably determined by determining a differential equation $dS(T)/dT$ of the measured turbidity level $S(T)$ after a certain length of time T after the mixing and setting the point when the polarity of the differential equation is reversed as the $T_{peak}$ and a measured turbidity level $S(T)$ at the time point as $S_{peak}$.

In another embodiment, when the $T_{peak}$ is a given value $T_0$ or smaller, the concentration of the analyte contained in the sample solution is preferably judged to be equal to or greater than a given value $C_0$.

The analyte is preferably human serum albumin.

The antibody is preferably a monoclonal antibody. The reagent preferably contains at least two monoclonal antibodies. It is preferred that the at least two monoclonal antibodies specifically bind to different binding sites of human serum albumin.

The sample solution is preferably urine.

The present invention further relates to an apparatus for turbidimetric immunoassay for performing the above-described turbidimetric immunoassay.

The apparatus for turbidimetric immunoassay according to one embodiment of the present invention comprises: a light source for directing light to the sample solution; a sample cell for holding the sample solution such that the light passes through the sample solution; a first optical sensor for detecting transmitted light passing through the sample solution and/or a second optical sensor for detecting scattered light generated during the propagation of the light through the sample solution; a mixer for mixing said sample solution with said reagent containing an antibody in said sample cell; and a computer for controlling the mixer and analyzing output signals sent from the first optical sensor and/or the second optical sensor.

In the apparatus, the concentration of an antigen contained in the sample solution is determined from the output signals sent from the first optical sensor and/or the second optical sensor after mixing the solution with the reagent.

The apparatus for turbidimetric immunoassay according to another embodiment of the present invention comprises: a light source for directing light to the sample solution; a sample cell for holding the sample solution such that the light passes through the sample solution; a first optical sensor for detecting transmitted light passing through the sample solution and/or a second optical sensor for detecting scattered light generated during the propagation of the light through the sample solution; a first differentiator for differentiating output signals sent from the first optical sensor and/or a second differentiator for differentiating output signals sent from the second optical sensor; a mixer for mixing said sample solution with said reagent containing an antibody in said sample cell; and a computer for controlling the mixer and analyzing the output signals from the first optical sensor, the second optical sensor, the first differentiator and/or the second differentiator.

In the apparatus, the concentration of an antigen contained in the sample solution is determined from the output signals sent from the first differentiator and/or the second differentiator after mixing the solution with the reagent.

According to the present invention, it is possible to expand the measurable concentration range for an antigen contained in a sample solution without a step of dilution or the like. Its practical effect will be enormous, and efficiency of measurement and test, as well as labor savings, can be realized.

It is noted that the above mixer can be omitted.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 22 is a graph created by plotting the output signals from an optical sensor 5 after 300 seconds as the turbidity level on the vertical axis and the concentrations of the sample solutions on the horizontal axis.

FIG. 23 is a top plan view schematically illustrating an apparatus for turbidimetric immunoassay according to another embodiment of the present invention.

FIG. 24 is a graph showing the variation of SC45 (indicated by a dotted line) and that of SC90 (indicated by a solid line) versus time.

FIG. 25 is a graph showing the correlation between $T_{peak}$ and concentration.

DETAILED DESCRIPTION OF THE INVENTION

Figure 1:
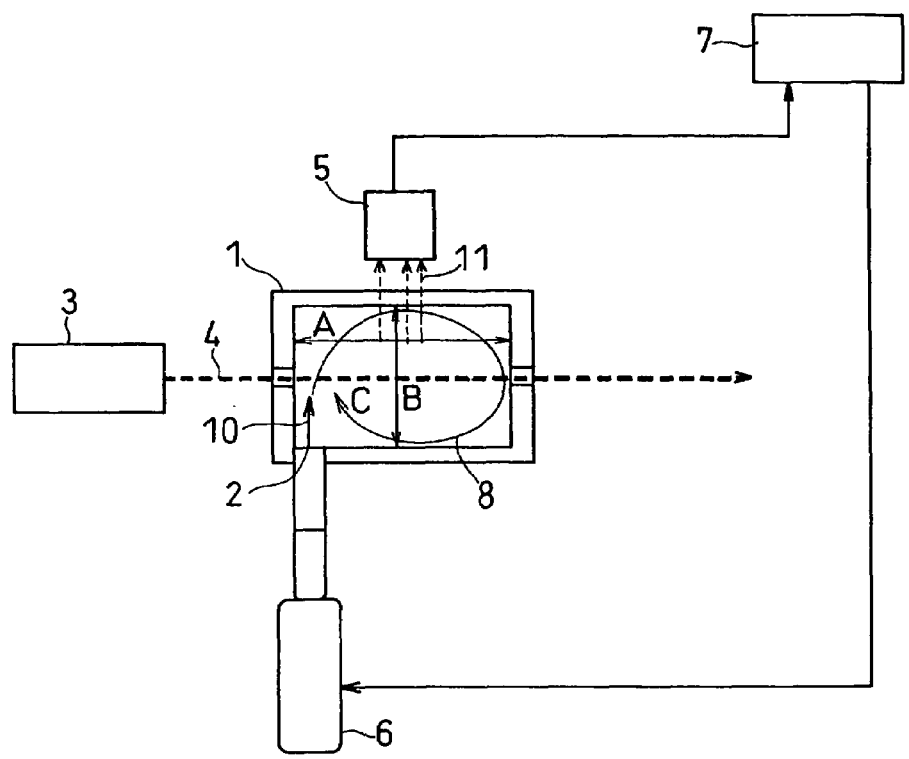
FIG. 1 is a top plan view schematically illustrating an apparatus for turbidimetric immunoassay according to one embodiment of the present invention.
Figure 2:
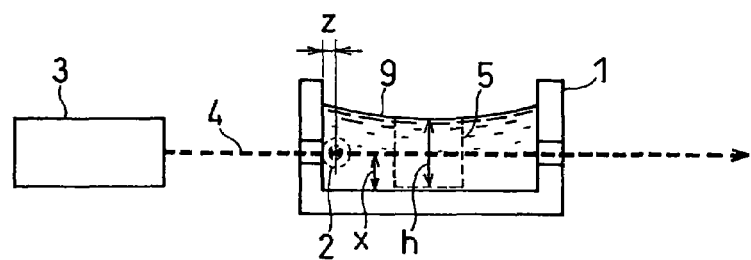
FIG. 2 is a schematic side view of an apparatus for turbidimetric immunoassay of FIG. 1.

A description is first given of a conventional turbidimetric immunoassay accompanied by the problems to be solved by the present invention. A turbidimetric immunoassay using an apparatus shown in FIGS. 1 and 2 is described here. FIG. 1 is a top plan view schematically illustrating the structure of an apparatus to be used in a conventional turbidimetric immunoassay and a turbidimetric immunoassay according to the present invention. FIG. 2 is a side view of an optical system in FIG. 1. A sample cell 1 shown in FIGS. 1 and 2 is a rectangular aluminum container having an opening at the top.

Glass plates serving as optical windows are embedded on both sides of the sample cell 1 so that light passes from one glass plate and to the other glass plate through a sample solution contained in the sample cell 1. A distance of the propagating direction of the light in the sample cell 1, that is, a distance between the optical windows, is represented by an arrow A, and a distance perpendicular to the propagating direction of the light is represented by an arrow B. Here, the explanation is given in the case of A=0.75 cm and B=0.4 cm.

An inlet 2 with a diameter (inner diameter) of 0.1 cm is located on the side face with no optical window of the sample cell 1 as seen from FIG. 1. The center of the inlet 2 is positioned a distance of x from the bottom of the sample cell 1 and a distance of z from one of the optical windows as shown in FIG. 2.

The feeding direction of a reagent indicated by an arrow 10 is parallel to the optical window and perpendicular to the optical axis of substantially parallel light 4, which will be described below. A placement like this creates, in the solution of the sample cell 1, an intersection point where a feeding axis extending from the center of the inlet 2 to the feeding direction and the optical axis of substantially parallel light 4 intersect each other. Here, x=0.15 cm and y=0.1 cm.

This apparatus includes, as a light source, a semiconductor laser module 3 for emitting substantially parallel light 4 having a wavelength of 780 nm, an intensity of 3.0 mW and a beam diameter of 0.12 cm. The optical axis of this substantially parallel light 4 is parallel to the bottom of the sample cell 1 and is positioned a distance of 0.4 cm from the bottom, which means the optical axis and the inlet 2 are positioned almost at the same height from the bottom.

An optical sensor 5 detects scattered light 11 generated during the propagation of the substantially parallel light 4 through the sample solution. A mixer 6 injects a reagent into a sample solution in the sample cell 1 through the inlet 2. A computer 7 analyzes output signals sent from the optical sensor 5 as well as controls the mixer 6.

In FIG. 1, the reference number 8 schematically indicates a vortex that occurs when the reagent is injected from the inlet 2. The reference number 9 indicates the surface of the sample solution, the lowest point of which is positioned a distance of h from the bottom of the sample cell 1.

In this sample cell 1, corners of the internal walls are curved. In other words, technically, the angles of the corners are not right angles so that the sample cell 1 will hold about 0.23 ml of liquid if h=8 cm. The surface of the sample solution herein which is denoted by the reference number 9 means the lowest point of the surface of the sample solution. According to this definition, the feeding direction is parallel to the surface of the sample solution in this embodiment.

A description is now given of the procedure for determining the concentration of human serum albumin contained in urine in the case of using the apparatus described above and urine as the sample solution.

First of all, urine determined to have a human serum albumin concentration of not greater than 0.03 mg/dl is prepared as the solvent. Human serum albumin is added to this solvent to prepare sample solutions with different concentrations: 1 mg/dl, 3 mg/dl, 5 mg/dl, 10 mg/dl, 15 mg/dl, 20 mg/dl, 30 mg/dl, 50 mg/dl and 100 mg/dl.

In order to formulate a neutral reaction system, a MOPS buffer solution with a pH of 7.4 is prepared using 0.05 M of MOPS (morpholinepropanesulfonic acid) and 4 wt % of polyethylene glycol 6000.

A rabbit-derived polyclonal human albumin antibody is dissolved in 0.05 M of a MOPS aqueous solution with a pH of 7.4 to prepare a reagent (antibody aqueous solution) with an antibody concentration of 2.5 mg/dl.

Then, 9 μl of the sample solution with a human serum albumin concentration of 0 mg/dl (i.e. urine used as the solvent above) is introduced into the sample cell 1. Subsequently, 145 μl of the MOPS buffer solution is introduced into the sample cell 1, followed by stirring. Note that the urine used here should be regarded as urine substantially having a human serum albumin concentration of 0 mg/dl because no human serum albumin is added thereto.

Figure 18:
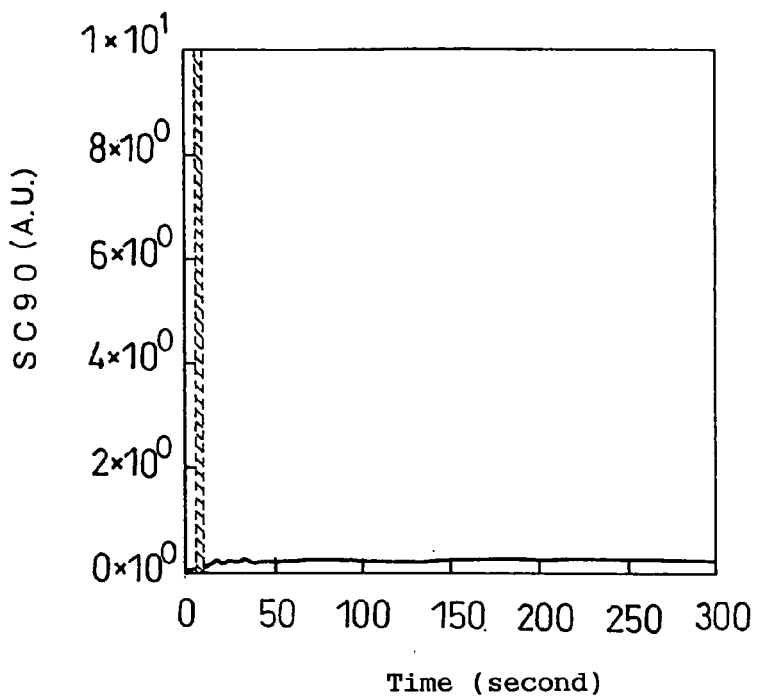
FIG. 18 is a graph showing the variation in output signal from an optical sensor 5 with time.

The computer 7 starts recording output signals sent from the optical sensor 5 at this time. FIG. 18 shows the variation of the output signal from the optical sensor 5 with time since the start. The horizontal axis represents the elapsed time after the start of recording the output signal, and the vertical axis represents the output signal (hereinafter referred to as "SC90") from the optical sensor 5 in FIG. 18. "SC90" is named because scattered light propagating at 90 degrees relative to the propagating direction of the substantially parallel light 4 of the light scattered in the sample solution is detected by the optical sensor 5.

After a lapse of 5 seconds, the computer 7 controls the mixer 6, such as a pipetter or pump, to allow 40 μl of the reagent (antibody aqueous solution) to be injected from the inlet 2 into the sample cell 1 for about 3 seconds.

The flow of the injected reagent obstructs the optical path of the substantially parallel light 4 during a period of about 3 seconds from the start of the injection of the reagent (i.e. from 5 seconds after the injection of the buffer solution) to disturb the intensity and the propagating direction of the transmitted light, which results in widely varied output signals of the optical sensor 5. The range in which the output signals vary as described above is indicated by the hatch pattern in FIG. 18.

Likewise, the sample solutions with different human serum albumin concentrations (1 mg/dl, 3 mg/dl, 5 mg/dl, 10 mg/dl, 15 mg/dl, 20 mg/dl, 30 mg/dl, 50 mg/dl and 100 mg/dl) are put into the same procedure as described above.

Figure 19:
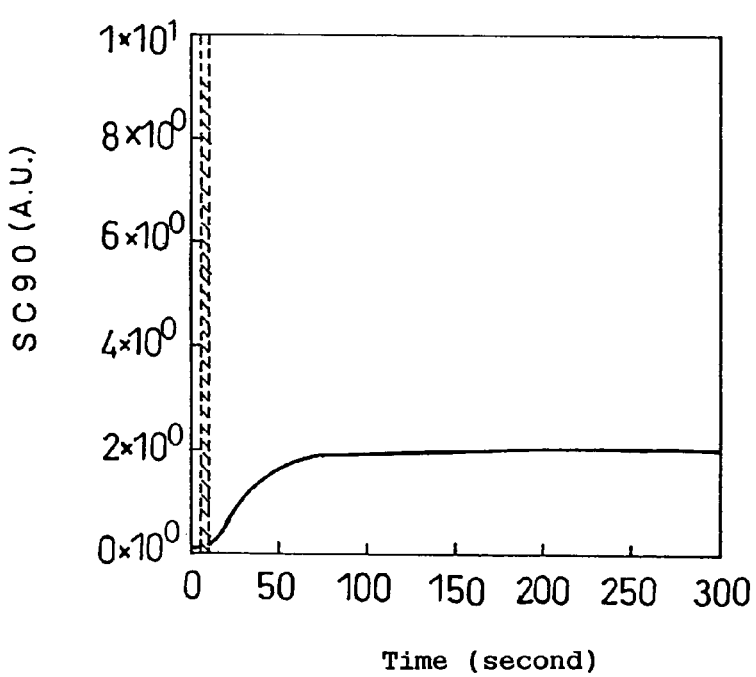
FIG. 19 is a graph showing the variation in output signal from an optical sensor 5 with time.
Figure 20:
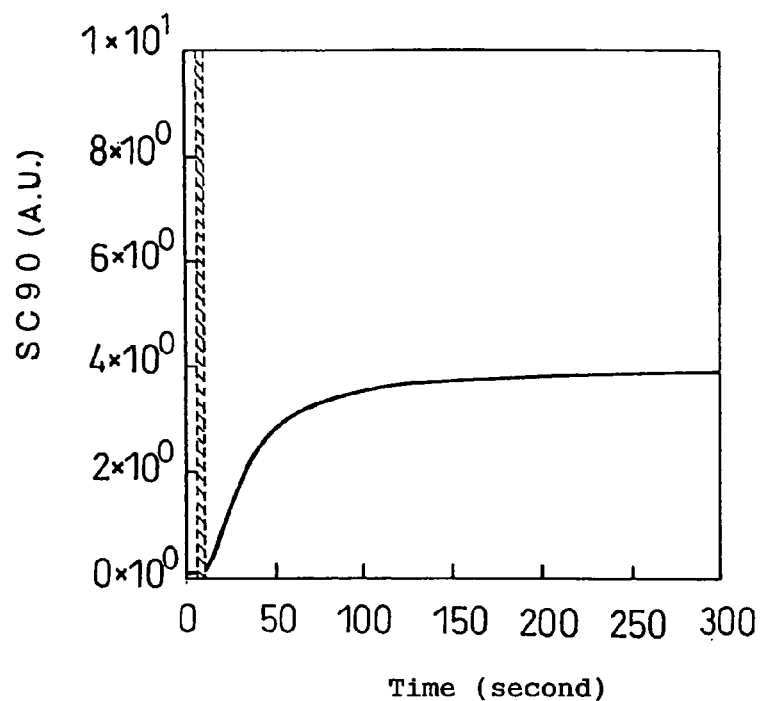
FIG. 20 is a graph showing the variation in output signal from an optical sensor 5 with time.
Figure 21:
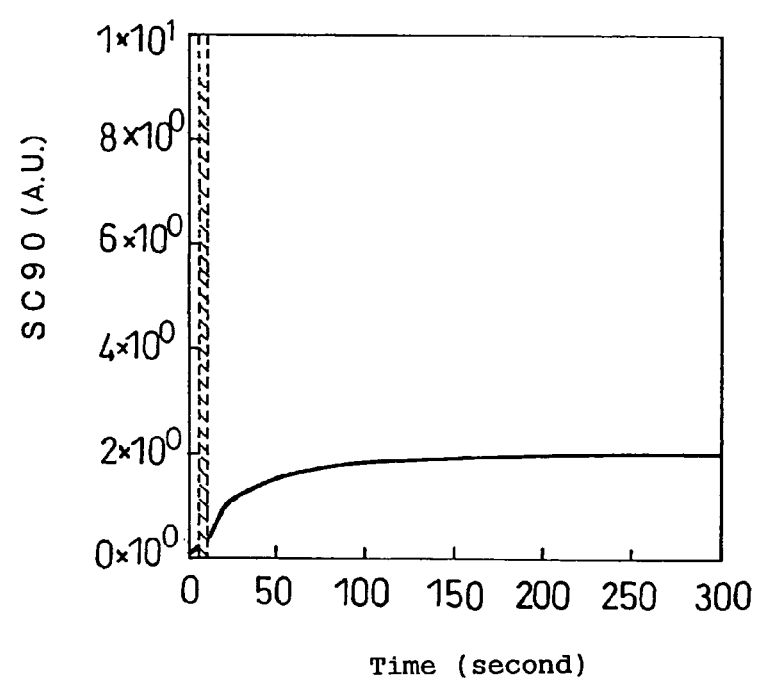
FIG. 21 is a graph showing the variation in output signal from an optical sensor 5 with time.

FIGS. 19 to 21 show the variation in the output signal from the optical sensor 5 with time for each of the sample solutions respectively having human serum albumin concentrations of 3 mg/dl, 10 mg/dl and 100 mg/dl. Similar to FIG. 18, the range in which the output signals vary widely is indicated by the hatch pattern in FIGS. 19 to 21.

As is obvious from FIGS. 18 to 21, the output signals of the optical sensor 5, which indicate turbidity, are saturated after 300 seconds. On the basis of the above, a graph shown in FIG. 22 is created by plotting the output signals from the optical sensor 5 as the turbidity level on the vertical axis and the concentration of the sample solutions on the horizontal axis.

Figure 17:
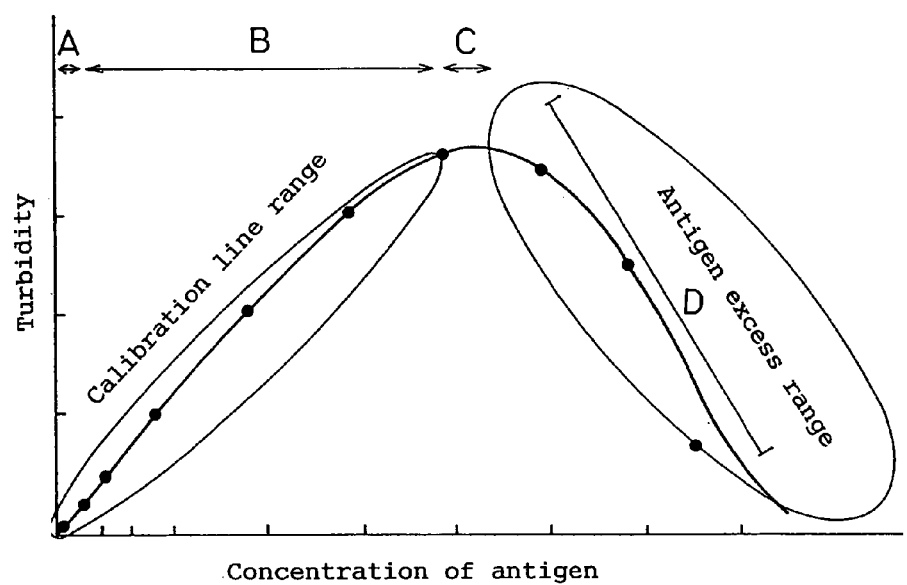
FIG. 17 is a graph showing the correlation between antigen concentration and turbidity level.

It is evident from FIG. 22 that the concentration range between 0 to 30 mg/dl corresponds to the A-B range of FIG. 17, that around 50 mg/dl corresponds to the C range of the same and that around 100 mg/dl corresponds to the D range of the same.

In FIG. 22, the concentration can be determined by making a calibration curve using turbidity levels at the concentration range of 0 to 30 mg/dl.

When the sample solution has a concentration of about not less than 50 mg/dl, however, the concentration may not be unambiguously determined only from the turbidity level after a certain period of time after mixing of the sample solution with the reagent because of the prozone phenomenon. For example, when the turbidity level (output signal from the optical sensor 5 after 300 seconds) is 7.5, it is difficult to identify whether the concentration of the sample solution is either about 20 mg/dl or 50 to 100 mg/dl.

It is therefore necessary to check that the sample solution has a human serum albumin concentration of not greater than 50 mg/dl by some way. In other words, the measurable concentration range for the antigen in the sample solution is limited to not greater than 50 mg/dl in the above-described method.

In view of the foregoing, the present invention has an object of solving the problem encountered in the turbidimetric immunoassay described above and expanding the measurable concentration range for an antigen in a sample solution without sacrifice of sensitivity in a low concentration range. The present invention has another object of providing a turbidimetric immunoassay free of a step of diluting a sample solution or a step of adding additional amount of antibody for checking that the concentration of the antigen is not in the postzone, that is, the concentration thereof is not in the D range of FIG. 17.

To be more specific, in the turbidimetric immunoassay of the present invention, the above problem resulting from the prozone phenomenon are avoided by performing the steps of:

(1) mixing the sample solution with the reagent to give a mixed solution;
(2) measuring the turbidity level of the mixed solution discretely a plurality of times or consecutively;
(3) determining the correlation between measured turbidity levels and time elapsed after the mixing; and
(4) detecting the maximum or minimum value of the measured turbidity level ($S_{peak}$) based on the aforesaid correlation to determine elapsed time when the $S_{peak}$ is observed ($T_{peak}$).

EMBODIMENT 1

This embodiment is an example of determining the concentration of albumin in urine by using a monoclonal antibody that specifically binds to human serum albumin and urine as the sample solution.

In turbidimetric immunoassay, it is crucial that an antigen and an antibody be aggregated by an antigen-antibody reaction. In other words, an antigen and an antibody should bind each other to produce bound substances, which are cross-linked between antibody molecules of the bound substances to produce larger particles (antigen-antibody complex). Accordingly, at least two different antibodies having different binding sites on the antigen are necessary.

The antigen-antibody complex should have a particle size enough to indicate the maximum or minimum value of the measured turbidity level. The size varies depending on various conditions, but preferred is about not less than 25 µm.

For this reason, a polyclonal antibody is typically used in turbidimetric immunoassay. It has been found, however, that even when a reagent prepared by mixing a plurality of monoclonal antibodies having different binding sites is used the antigen and the antibodies are aggregated to produce an antigen-antibody complex, and the concentration of antigen can be determined by turbidimetric immunoassay. Moreover, the expansion of measurable concentration range has been achieved by observing the transient phenomenon of turbidity produced by mixing a sample solution with a reagent containing a plurality of monoclonal antibodies having different binding sites, followed by analysis thereof.

A specific example is given below using FIGS. 1 to 22. FIGS. 1 and 2 are exactly the same as used in the conventional technology described above, and the apparatus operates in the same manner as described above. In this embodiment, the concentration of human serum albumin in urine was determined by using the apparatus and urine as the sample solution.

Similar to the conventional technology, urine determined to have a human serum albumin concentration of not greater than 0.03 mg/dl was prepared as the solvent. Human serum albumin was added to the solvent to prepare sample solutions with different concentrations: 3 mg/dl, 5 mg/dl, 10 mg/dl, 30 mg/dl, 50 mg/dl, 100 mg/dl, 150 mg/dl, 250 mg/dl, 300 mg/dl and 500 mg/dl.

For the preparation of a buffer solution for obtaining a neutral reaction system, similar to the conventional technology, MOPS was used, and its concentration and pH of the buffer solution were adjusted to those typically used. A MOPS buffer solution with a pH of 7.4 containing 0.05 M of MOPS and 4 wt % of polyethylene glycol 6000 was prepared.

Then, three types (AHSA1, AHSA2 and AHSA3) of mouse-derived monoclonal antibodies that specifically bind to different binding sites of human serum albumin were prepared. AHSA1, AHSA2 and AHSA3 are monoclonal antibodies produced from cell strains having been deposited with the International Patent Organism Depositary, National Institute of Advanced Industrial Science and Technology under the accession numbers FERM BP-8308, FERM BP-8309 and FERM BP-7938.

The three types of monoclonal antibodies were dissolved in the MOPS buffer solution prepared above in a molar ratio of 1:1:8 (molar concentration of AHSA1:that of AHSA2:that of AHSA3) to give a reagent (antibody aqueous solution). The total concentration of the three antibodies was 2.4 mg/dl.

In the same manner as in the conventional technique, 9 µl of the sample solution with different human serum albumin concentrations (0 mg/dl, 3 mg/dl, 5 mg/dl, 10 mg/dl, 30 mg/dl, 50 mg/dl, 100 mg/dl, 150 mg/dl, 250 mg/dl, 300 mg/dl and 500 mg/dl) was introduced into the sample cell 1. Subsequently, 145 µl of the reagent was introduced into the sample cell 1, followed by stirring. Note that the sample solution with a human serum albumin concentration of 0 mg/dl was urine used as the solvent above and human serum albumin was not added thereto so that it should be regarded as sample substantially with a human serum albumin concentration of 0 mg/dl.

The computer 7 started recording output signals sent from the optical sensor 5 at this time. FIGS. 3 to 13 show the variation in the output signal from the optical sensor 5 with time since the start for each of the sample solutions. The horizontal axis represents the elapsed time after the start of recording the output signal, and the vertical axis represents the output signal (hereinafter referred to as "SC90") from the optical sensor 5 in FIGS. 3 to 13. After a lapse of 5 seconds, the computer 7 controlled the mixer 6 to allow 40 µl of the reagent (antibody aqueous solution) to be injected from the inlet 2 into the sample cell 1 for about 3 seconds.

During a period of about 3 seconds from the start of the injection of the reagent (i.e. from 5 seconds after the injection of the buffer solution), the flow of the injected reagent obstructed the optical path of the substantially parallel light 4 to disturb the intensity and the propagating direction of the transmitted light, and therefore the output signals from the optical sensor 5 were widely varied. The range in which the output signals widely varied is indicated by the hatch pattern in FIGS. 3 to 13.

Figure 3:
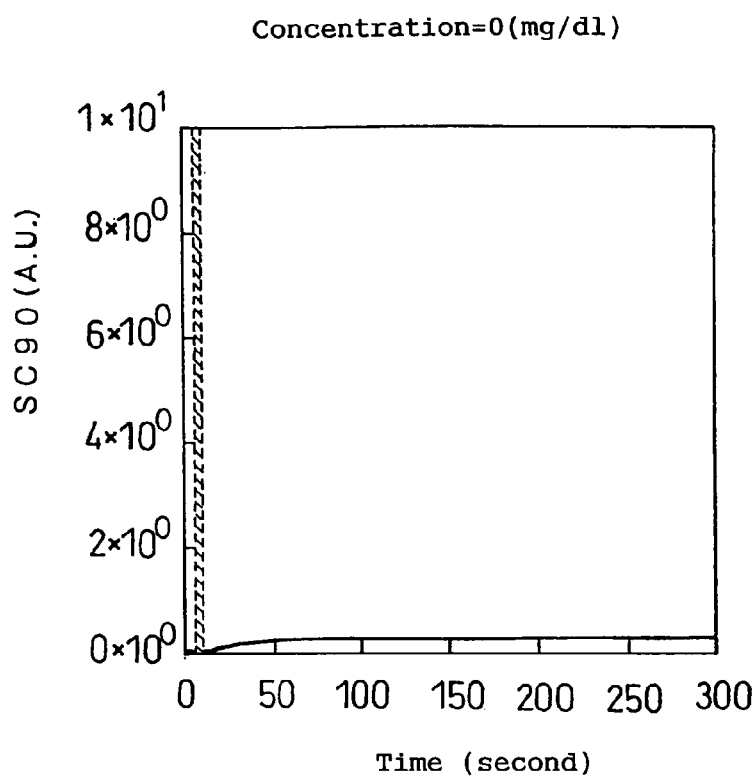
FIG. 3 is a graph showing the variation in output signal from an optical sensor 5 in EMBODIMENT 1 with time.
Figure 4:
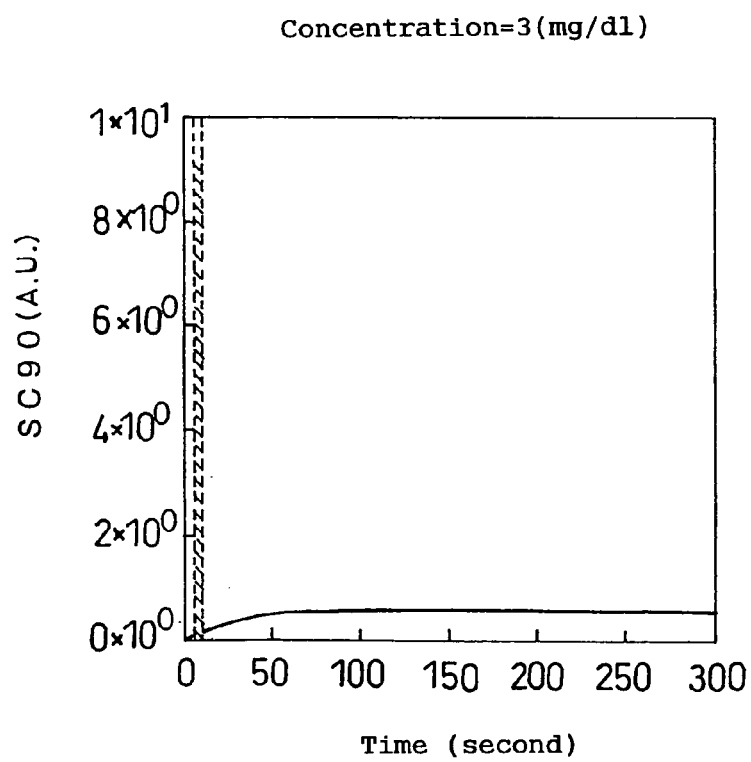
FIG. 4 is a graph showing the variation in output signal from an optical sensor 5 in EMBODIMENT 1 with time.
Figure 5:
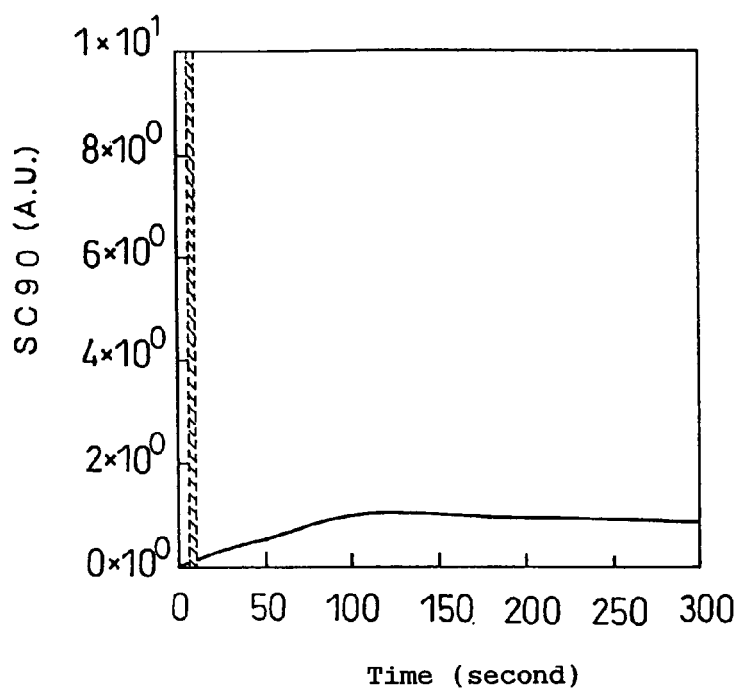
FIG. 5 is a graph showing the variation in output signal from an optical sensor 5 in EMBODIMENT 1 with time.

In FIGS. 3 and 4 showing the correlation between the elapsed time after addition of the reagent and the output signal from the optical sensor 5 for sample solutions with concentrations of 0 and 3 mg/dl, the output signal increased monotonously and was saturated at a certain level after 300 seconds.

Unlike the above two graphs, in FIGS. 5 to 13 for sample solutions with concentrations of 5 mg/dl, 10 mg/dl, 30 mg/dl, 50 mg/dl, 100 mg/dl, 150 mg/dl, 250 mg/dl, 300 mg/dl and 500 mg/dl, the output signal from the optical sensor 5 abruptly increased to the maximum after addition of the reagent, and then decreased monotonously. After 300 seconds, the output signal was saturated at a certain level.

Figure 14:
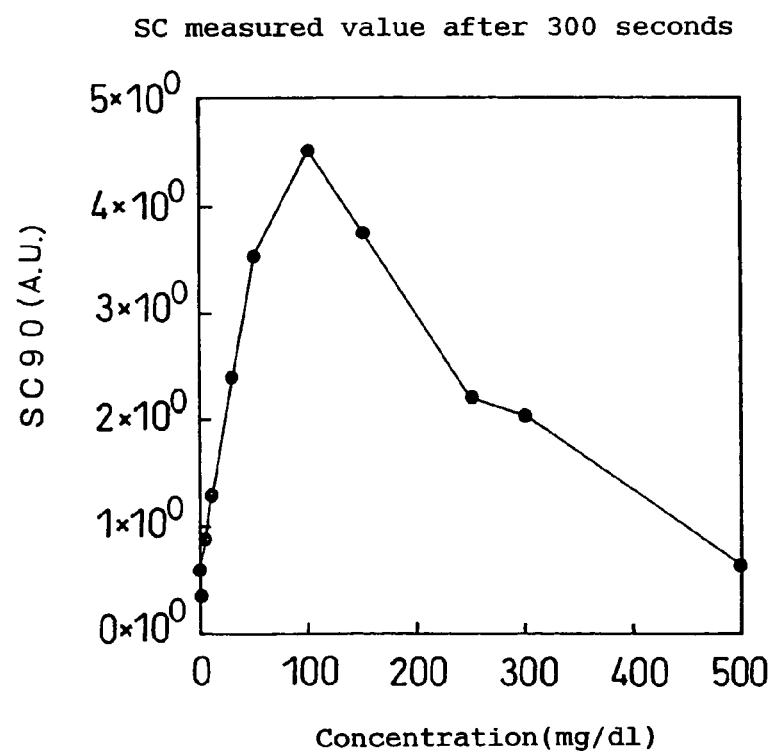
FIG. 14 is a graph created by plotting the output signals from an optical sensor 5 after 300 seconds as the turbidity level on the horizontal axis and the concentrations of the sample solutions on the vertical axis.

A graph shown in FIG. 14 was created by plotting the output signals of the optical sensor 5 after 300 seconds of the sample solutions with concentrations of 0 mg/dl, 3 mg/dl, 5 mg/dl, 10 mg/dl, 30 mg/dl, 50 mg/dl, 100 mg/dl, 150 mg/dl, 250 mg/dl, 300 mg/dl and 500 mg/dl as the turbidity level on the vertical axis and the concentrations of the sample solutions on the horizontal axis. It is clear from FIG. 14 that the concentration range between 0 to 50 mg/dl corresponds to the A-B range of FIG. 17, that around 100 mg/dl corresponds to the C range of the same and that after 150 mg/dl corresponds to the D range of the same.

In FIG. 14, the concentration can be determined by constructing a calibration curve using turbidity levels at the concentration range of 0 to 50 mg/dl. When the sample solution has a concentration of about not less than 100 mg/dl, however, the concentration may not be unambiguously determined only from the turbidity level after a certain period of time after mixing of the sample solution with the reagent because of the prozone phenomenon. For example, when the turbidity level (output signal from the optical sensor 5 after 300 seconds) is 2.4, it is difficult to identify whether the concentration of the sample solution is either about 30 mg/dl or 150 to 250 mg/dl. It is therefore necessary to check that the sample solution has a human serum albumin concentration of not greater than 100 mg/dl by some way. In other words, the measurable concentration range for the antigen in the sample solution is limited to not greater than 100 mg/dl in the above-described method.

As stated above, similar to the conventional technique, the concentration sometimes cannot be unambiguously determined only from the turbidity level after a certain period of time after mixing of the sample solution with the reagent (FIG. 14) because of the prozone phenomenon. The measurable concentration range of the antigen is limited.

Figure 15:
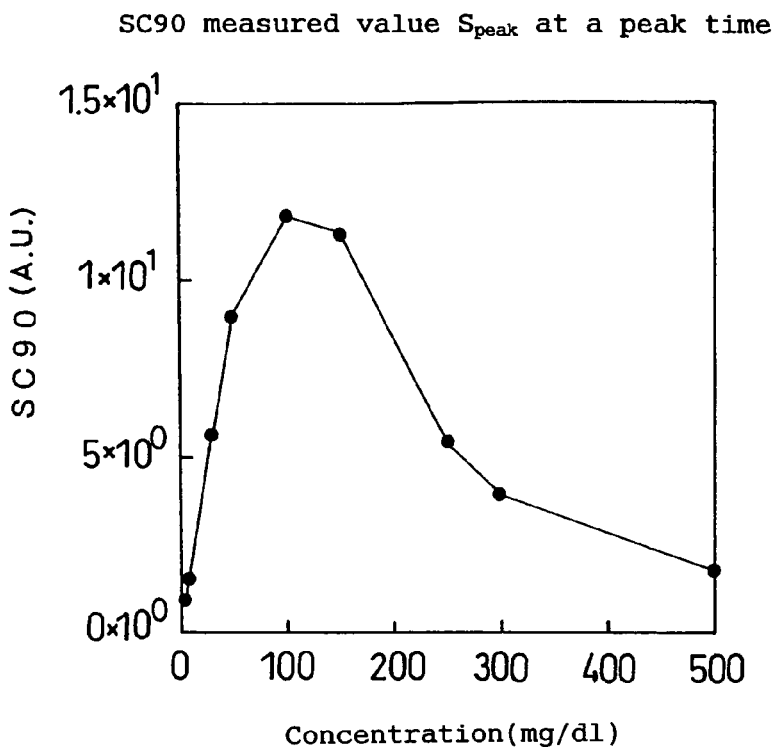
FIG. 15 is a graph created by plotting the concentrations of sample solutions of FIGS. 5 to 13 on the horizontal axis and the maximum values of turbidity level on the vertical axis.

Given the above, the transient phenomenon of the turbidity after mixing of the sample solution with the reagent was analyzed as follows. FIG. 15 was first created by plotting the concentrations of the sample solutions of FIGS. 5 to 13 on the horizontal axis and the maximum values of the turbidity level ($S_{peak}$) on the vertical axis.

Figure 16:
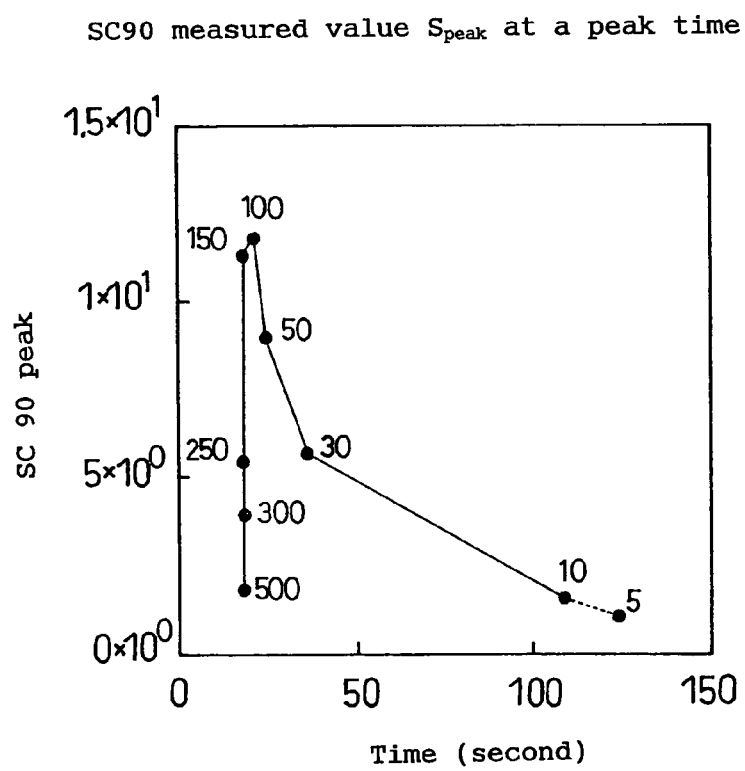
FIG. 16 is a graph created by plotting the elapsed time when the maximum value is observed ($T_{peak}$) on the horizontal axis and the maximum values of turbidity level ($S_{peak}$) on the vertical axis.

FIG. 16 was then created by plotting the elapsed time when the maximum value was observed ($T_{peak}$) on the vertical axis and the maximum value of the turbidity level ($S_{peak}$) on the vertical axis. The number next to each of the dots in FIG. 16 indicates concentration (mg/dl). It is apparent from FIG. 16 that as the concentration was increased the elapsed time when the maximum value was observed became shorter, and when the concentration was not less than 100 mg/dl, the elapsed time is asymptotic to about 18 seconds.

It has been found that the measurable concentration range for the antigen in the sample solution can be expanded by utilizing FIG. 16 in addition to FIG. 14. For instance, when the turbidity level (output signal from the optical sensor 5 after 300 seconds) is 2.4, it is difficult to identify whether the concentration of the antigen in the sample solution is either about 30 mg/dl or 150 to 250 mg/dl. With the use of FIG. 16 in addition to FIG. 14, however, it is possible to identify and determine the concentration. To be more specific, if the elapsed time when the maximum value is observed in this case is about 35 seconds, the concentration can be determined to 30 mg/dl. If the elapsed time when the maximum value is observed is about 18 seconds, the concentration can be determined to 150 to 250 mg/dl. As just described, the concentration can be unambiguously determined from the correlation between the turbidity level after a certain period of time after mixing of the sample solution with the reagent (FIG. 14) and the elapsed time when the maximum value is observed ($T_{peak}$). In an example given here, the measurable concentration range for the antigen in the sample solution was successfully expanded.

As described above, the determination of the concentration of the antigen in the sample solution was achieved by determining the correlation between the maximum value of the measured turbidity level ($S_{peak}$) and elapsed time when the maximum value was observed ($T_{peak}$) and then the correlation between the elapsed time $T_{peak}$ and the measured turbidity level $S(T)$ after a certain length of time T after the mixing.

When the concentration is as low as 0 or 3 mg/dl, however, the maximum value of the measured turbidity level does not exist. Such case is deemed to be in the A-B range (i.e. prozone) of FIG. 17. Therefore, the concentration can be unambiguously determined only from the measured turbidity $S(T)$ after a certain period of time T.

Here, it is preferred that time T satisfies the relation of $T>T_{peak}$. If the relation is satisfied, reproducibility is improved. Further, time T is the time when S is saturated. On the other hand, it is also preferred that time T satisfies the relation of $T<T_{peak}$. If this relation is satisfied, a concentration can be determined in a shorter measurement time.

In this embodiment, the turbidity level was measured by detecting scattered light, but it may be measured by detecting transmitted light. In this case, $S_{peak}$ should be the minimum value of transmitted light intensity and $T_{peak}$ should be the elapsed time when the minimum value is observed to obtain the same effect as above because turbidity varies inversely to the intensity of transmitted light.

Further, it is also possible to improve the reliability of the measurement by detecting both scattered light and transmitted light and comparing the obtained results.

EMBODIMENT 2

A description is given of a second embodiment according to the present invention referring to FIG. 15. In this embodiment, an example of determining the concentration using FIGS. 15 and 16 is shown.

When the maximum value of the turbidity level is 5.5, for example, it is difficult to identify, from FIG. 15 only, whether the sample solution has a concentration of either about 30 mg/dl or 150 to 250 mg/dl, but with the use of FIG. 16 in addition to FIG. 15 the concentration can be identified and determined. To be more specific, if the elapsed time when the maximum value is observed ($T_{peak}$) in this case is about 35 seconds, the concentration can be determined to 30 mg/dl. If the elapsed time when the maximum value is observed ($T_{peak}$) is about 18 seconds, the concentration can be determined to 150 to 250 mg/dl.

As just described, the concentration can be unambiguously determined from the correlation between the maximum value ($S_{peak}$) of the turbidity level after a certain period of time after mixing of the sample solution with the reagent (FIG. 15) and the elapsed time when the maximum value is observed ($T_{peak}$) In an example given here, the measurable concentration range for the antigen in the sample solution was successfully expanded to 500 mg/dl.

This embodiment is more advantageous than EMBODIMENT 1 in speeding up the measurement because the concentration can be determined right after the maximum value of the turbidity level is detected. In the case where the concentration is so low that the maximum value does not exist, however, the concentration should be determined by the turbidity level after a certain period of time. Enormous effect can be obtained by using this embodiment with EMBODIMENT 1.

EMBODIMENT 3

A description is given of a third embodiment according to the present invention referring to FIG. 16. As seen from FIG.

16, when the elapsed time when the maximum value is observed ($T_{peak}$) is not less than a given value $T_0$ ($T_0 \approx 18$ seconds in FIG. 16), the concentration can be unambiguously determined from the $T_{peak}$ only. To sum up, when the elapsed time ($T_{peak}$) is not greater than a given value $T_0$, the concentration can be determined to be equal to or greater than a given value $C_0$ ($C_0$ is 100 mg/dl in FIG. 16). Conversely, when the elapsed time ($T_{peak}$) is not less than a given value $T_0$, the concentration can be found from FIG. 16, in other words, it can be determined according to $T_{peak}$ in FIG. 16. This embodiment is also more advantageous than EMBODIMENT 1 in speeding up the measurement because the concentration can be determined right after the maximum value of the turbidity level is detected.

In the case where the concentration is so low that the maximum value does not exist, however, the concentration should be determined by the turbidity level after a certain period of time. Enormous effect can be obtained by using this embodiment with EMBODIMENT 1.

EMBODIMENT 4

A description is given of a fourth embodiment according to the present invention referring to FIG. 23. FIG. 23 shows another embodiment of an apparatus for turbidimetric immunoassay that can be used in the present invention. The structural elements indicated by the reference numbers 1 to 11 in FIG. 23 are the same as those indicated by the reference numbers 1 to 11 in FIG. 1. The reference number 12 is a differentiator for differentiating the output signals from an optical sensor 5. The output signals from the differentiator 12 are analyzed by a computer 7. This apparatus can recognize the maximum value with high accuracy and speed because the maximum value is set when the sign of the output signal of the differentiator 12 is reversed.

As described above, according to this embodiment, it is possible to determine the concentration of the antigen with high speed when the sample solution containing the antigen at a low concentration is used because a smaller maximum value can be quickly recognized.

In order for the output signal from the optical sensor 5 representing the intensity of the scattered light denoted by SC90 to show its maximum value as described above, the antigen-antibody complex produced by the specific binding between the antigen and the antibodies should have a particle size larger than a given particle size.

This is closely related to the fact that scattered light intensity varies depending on the propagating direction of scattered light. When the particle size of the particles suspended in the solution is small enough compared to the wavelength of exciting light, which corresponds to the substantially parallel light 4, to be more specific, when the particle size is not greater than 1/20 of the wavelength, the distribution of scattered light intensity does not depend on its propagating direction.

As the particle size becomes larger, the intensity of forward-scattered light increases. The forward-scattered light herein means light scattered into directions that are at not greater than 90 degrees to the propagating direction of the exciting light. Also, an increase in the particle size of the antigen-antibody complex means a lower particle concentration.

From the above, SC90 once increases when the antigen-antibody complex grows as the antigen-antibody reaction proceeds. When the antigen-antibody complex further grows and its particle size becomes large, however, SC90 decreases because the intensity of forward-scattered light increases and the particle concentration decreases, which means the maximum value can be observed.

This phenomenon is described referring to FIG. 24. The vertical axis at the left represents the intensity of the scattered light that propagates at an angle of 45 degrees to the propagating direction of the substantially parallel light 4 among the scattered light generated in the solution.

This is the output signal sent from the optical sensor 5 when the optical sensor 5 of FIG. 1 is placed such that it can detect the scattered light that propagates at an angle of 45 degrees to the propagating direction of the substantially parallel light 4 among the scattered light generated in the solution, which is referred to as SC45 hereinafter. The SC45 in the case of the concentration of albumin being 10 mg/dl is indicated by a dotted line in FIG. 24.

Figure 6:
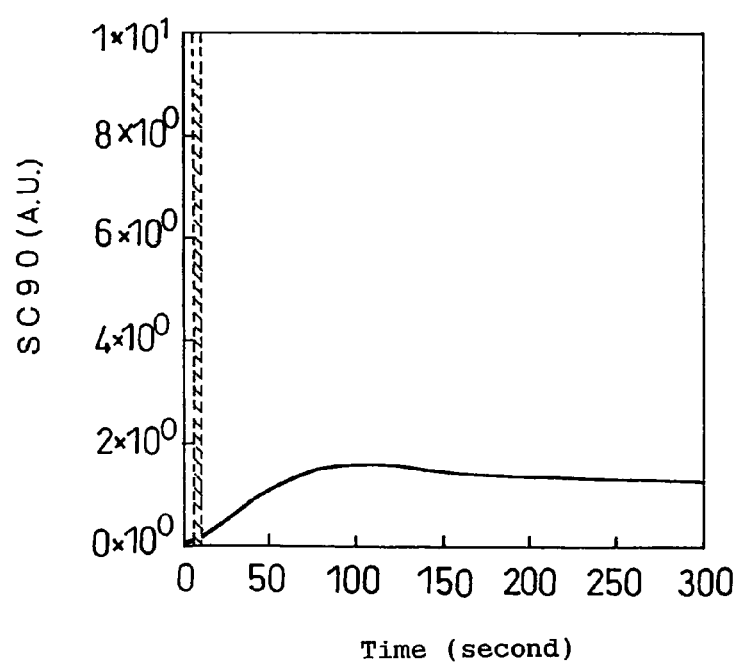
FIG. 6 is a graph showing the variation in output signal from an optical sensor 5 in EMBODIMENT 1 with time.
Figure 7:
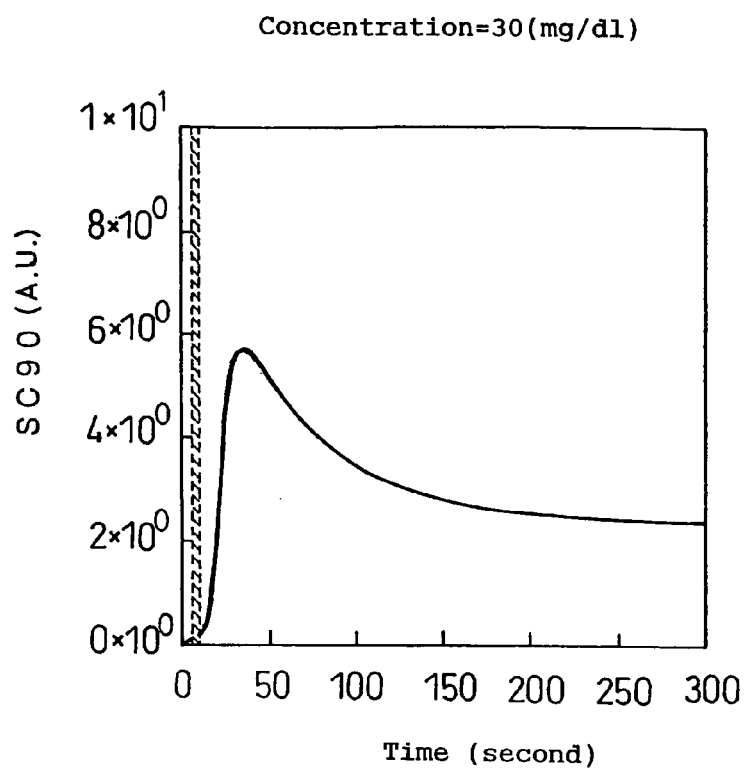
FIG. 7 is a graph showing the variation in output signal from an optical sensor 5 in EMBODIMENT 1 with time.
Figure 8:
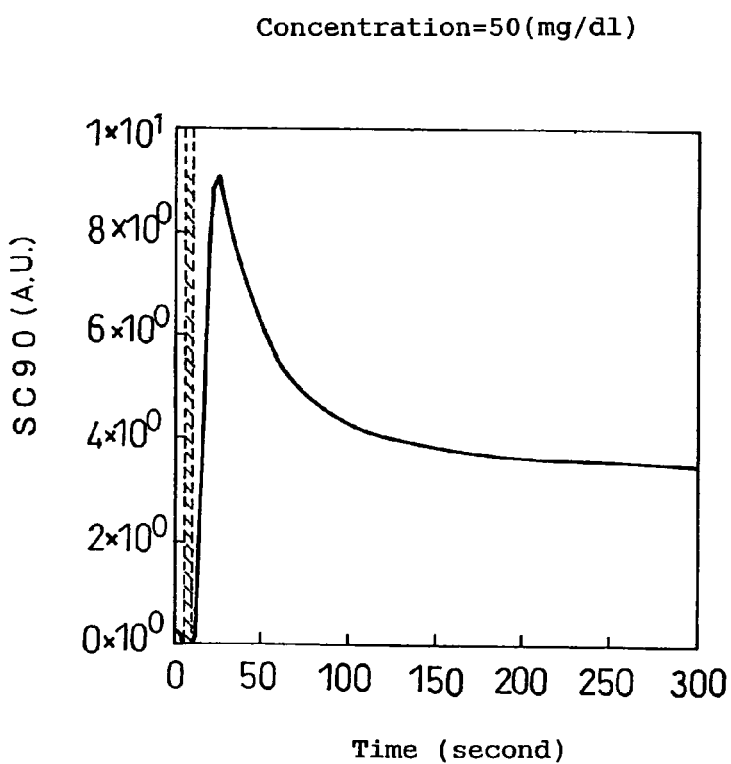
FIG. 8 is a graph showing the variation in output signal from an optical sensor 5 in EMBODIMENT 1 with time.
Figure 9:
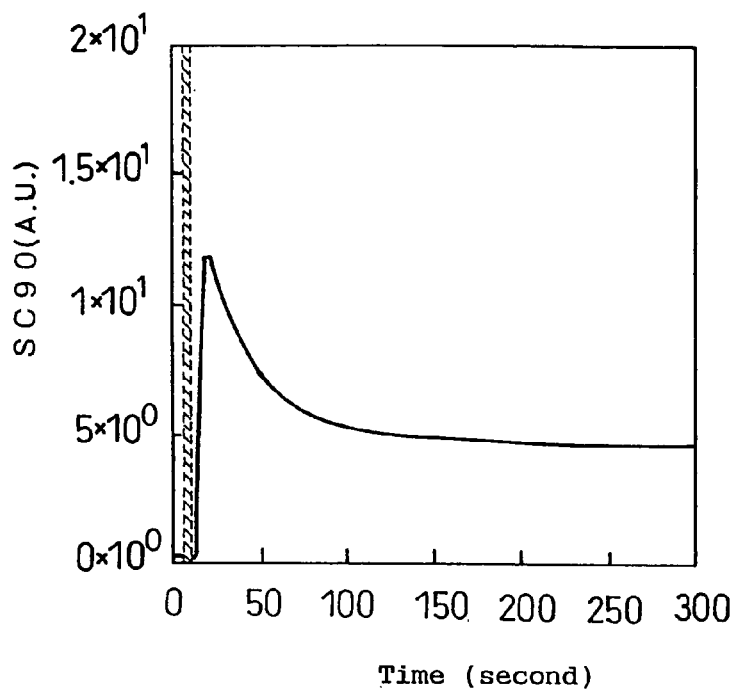
FIG. 9 is a graph showing the variation in output signal from an optical sensor 5 in EMBODIMENT 1 with time.
Figure 10:
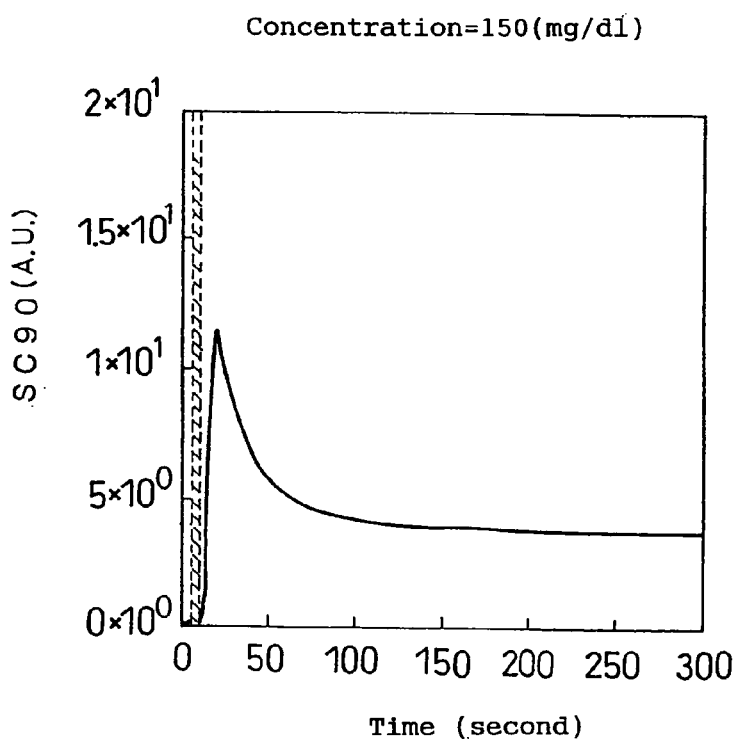
FIG. 10 is a graph showing the variation in output signal from an optical sensor 5 in EMBODIMENT 1 with time.
Figure 11:
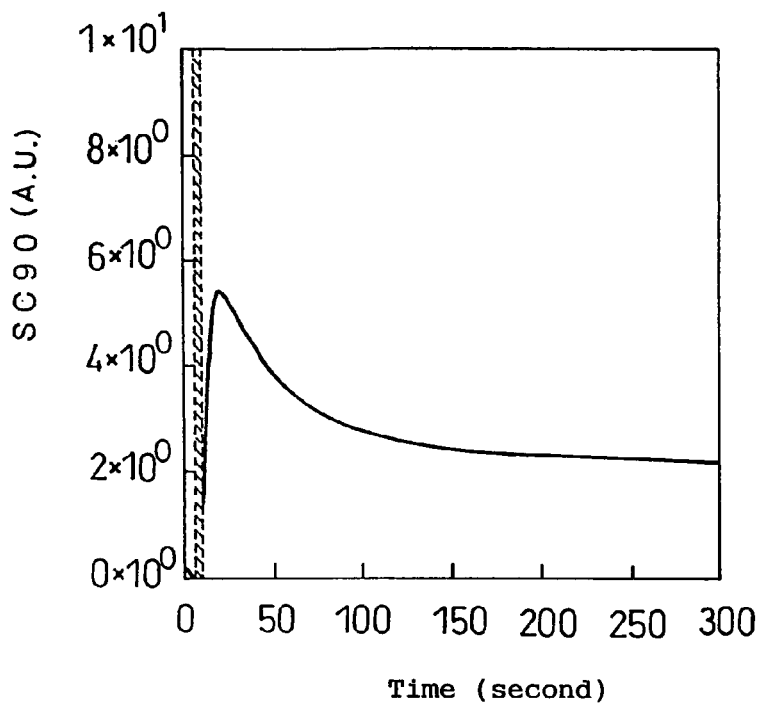
FIG. 11 is a graph showing the variation in output signal from an optical sensor 5 in EMBODIMENT 1 with time.
Figure 12:
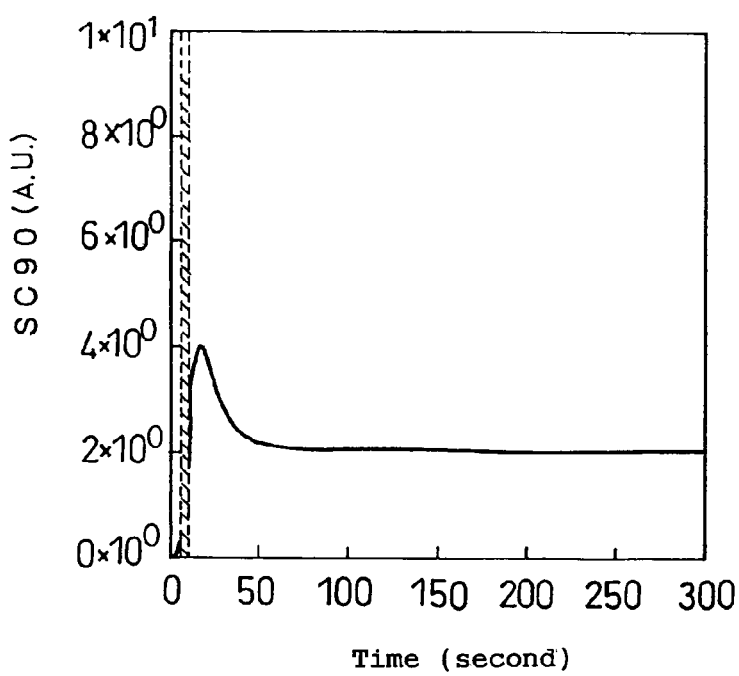
FIG. 12 is a graph showing the variation in output signal from an optical sensor 5 in EMBODIMENT 1 with time.
Figure 13:
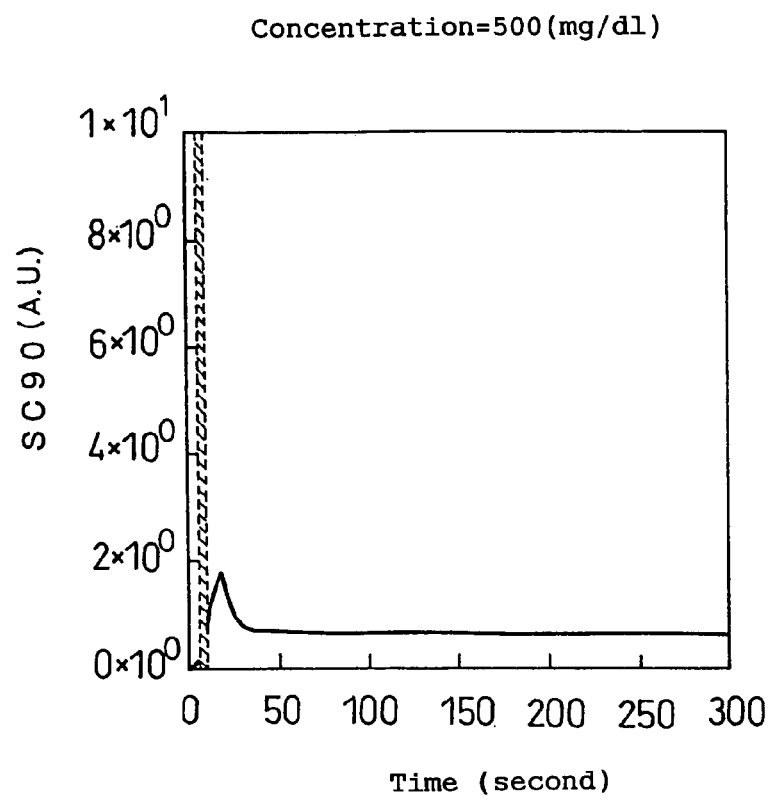
FIG. 13 is a graph showing the variation in output signal from an optical sensor 5 in EMBODIMENT 1 with time.

On the other hand, the signal of SC90 in the case stated above is indicated by a solid line in FIG. 24, which corresponds to that of FIG. 6. The conditions for the measurement for the dotted and solid lines are the same as those for FIG. 6. Incidentally, the absolute values of the vertical axis representing SC45 are arbitrary and do not correspond to FIG. 6. As is obvious from FIG. 24, SC45 continuously increases for 300 seconds, indicating that the antigen-antibody complex keeps growing.

In this case where the apparatus of FIG. 1 and the antibody combination described above were used, the particle size was about not less than 25 μm when the maximum value of SC90 was observed.

In the above EMBODIMENT 3, a graph indicating the correlation between the peak of SC90 and the elapsed time was shown in FIG. 16, but it is also possible to unambiguously determine the concentration only from $T_{peak}$ with the use of a graph showing the correlation between $T_{peak}$ and the concentration as shown in FIG. 25.

The turbidimetric immunoassay according to the present invention can be suitably used for urinalysis testing.

According to the present invention, it is possible to expand the measurable concentration range for an antigen contained in a sample solution without a step of dilution or the like. Its practical effect will be enormous, and efficiency of measurement and test, as well as labor savings, can be realized.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

The invention claimed is:

1. A turbidimetric immunoassay for quantifying a concentration of an analyte in a sample solution by mixing the sample solution containing an antigen as the analyte with a reagent containing an antibody that specifically binds to said analyte and detecting signals representing turbidity caused by an antigen-antibody complex produced by said specific binding reaction, said turbidimetric immunoassay comprising the steps of:

(1) mixing a plurality of solutions with different known concentrations of analyte and said reagent, respectively, to give a plurality of mixed solutions with different known concentrations of analyte;

(2) measuring the turbidity levels of said plurality of mixed solutions over time;

(3) determining for each said mixed solutions, the maximum value of said measured turbidity levels ($S_{peak}$), the elapsed time at which $S_{peak}$ is observed ($T_{peak}$), and the turbidity level at certain elapsed time T after the mixing, (S(T));
(4) creating a first calibration curve indicating a first correlation between said known concentrations of analyte and the turbidity levels S(T) detected in said step (3), and a second calibration curve indicating a second correlation between said maximum values of said measured turbidity levels ($S_{peak}$) detected in said step (3), said elapsed time at which $S_{peak}$ is observed ($T_{peak}$), and said known concentrations of analyte,
wherein said second calibration curve has the maximum value of said $S_{peak}$ ($Sm_{peak}$);
(5) after step (4), mixing said sample solution and said reagent to give a mixed sample solution;
(6) measuring the turbidity levels of said mixed sample solution over time;
(7) detecting for said mixed sample solution, the maximum value of the turbidity levels measured in said step (6) ($Ss_{peak}$), the elapsed time at which $Ss_{peak}$ is observed ($Ts_{peak}$), and the turbidity level Ss(T) of said mixed sample solution at the elapsed time T after the mixing;
(8) comparing said $Ts_{peak}$ with the $T_{peak}$ at which $Sm_{peak}$ is observed in said second calibration curve ($Tm_{peak}$);
(9) when said $Ts_{peak}$ is greater than said $Tm_{peak}$, converting said Ss(T) into the concentration of said analyte using said first calibration curve; and
(10) when said $Ts_{peaks}$ is equal to or smaller than said $Tm_{peak}$, determining the concentration of analyte to be equal to or greater than the concentration of analyte corresponding to $Sm_{peak}$ in said second calibration curve.

2. The turbidimetric immunoassay in accordance with claim 1, wherein said turbidity levels in said step (2) and step (6) are measured by scattered light.

3. The turbidimetric immunoassay in accordance with claim 1, wherein $T > T_{peak}$ is satisfied.

4. The turbidimetric immunoassay in accordance with claim 1, wherein said $S_{peak}$ as well as said $T_{peak}$ are determined by:
determining a differential equation dS(T)/dT of said measured turbidity level S(T) after a certain length of time T after said mixing;
setting T when a polarity of said differential equation is reversed as said $T_{peak}$; and
setting a measured turbidity level S(T) at said T as $S_{peak}$.

5. The turbidimetric immunoassay in accordance with claim 1, wherein said analyte is human serum albumin.

6. The turbidimetric immunoassay in accordance with claim 5, wherein said antibody is a monoclonal antibody, said reagent contains at least two monoclonal antibodies, and said at least two monoclonal antibodies specifically bind to different binding sites of human serum albumin.

7. The turbidimetric immunoassay in accordance with claim 6, wherein said sample solution is urine.

8. The turbidimetric immunoassay in accordance with claim 1, wherein $T = T_{peak}$ is satisfied.

* * * * *